United States Patent

Sukhova et al.

[11] 4,201,784
[45] May 6, 1980

[54] SUBSTITUTED 2-[2'-(5''-NITROFURYL-2'')VINYL-AND 4'-(5''-NITROFURYL-2'')-1,3-BUTADIERYL]-QUINOLINE-4-CARBOXYLIC ACID AMIDES AND SALTS THEREOF

[75] Inventors: Nina M. Sukhova; Marger J. Lidaka, ulitsa Mezhotnes, 37, kv. 1; Valentina A. Voronova; Aina A. Zidermane; Iya M. Kravchenko; Anda Z. Dauvarte; Ieva E. Preisa; Dainuvite V. Meirena, all of Riga, U.S.S.R.

[73] Assignee: Institut Organicheskogo Sinteza Akademii Nauk Latviiskoi SSR, Riga, U.S.S.R.

[21] Appl. No.: 940,798

[22] Filed: Sep. 7, 1978

[30] Foreign Application Priority Data

Sep. 9, 1977 [SU] U.S.S.R. ............................. 2524871

[51] Int. Cl.$^2$ ........................................... C07D 405/06
[52] U.S. Cl. ................................... 424/258; 542/411; 542/405
[58] Field of Search ................. 542/411, 405; 424/258

[56] References Cited

U.S. PATENT DOCUMENTS

| | | | |
|---|---|---|---|
| 3,658,796 | 4/1972 | Berger et al. | 542/411 |
| 3,660,384 | 5/1972 | Johnson | 542/411 |
| 3,994,882 | 11/1976 | Hirao et al. | 542/405 |

FOREIGN PATENT DOCUMENTS

| | | | |
|---|---|---|---|
| 4319547 | 8/1968 | Japan | 542/411 |
| 1065617 | 4/1967 | United Kingdom | 542/411 |

OTHER PUBLICATIONS

Miura et al., Chem. & Pharm. Bull. (Japan) 13 (1965), pp. 525–528.
Buttersworth, Progress in Medicinal Chem., vol. 5 (1967), 320–322, 330, 333, 335.
Wagner et al., Synthetic Organic Chemistry, John Wiley & Sons, N.Y., N.Y., 1955, pp. 546–547, 566–567.

Primary Examiner—Arthur P. Demers
Attorney, Agent, or Firm—Ladas, Parry, Von Gehr, Goldsmith & Deschamps

[57] ABSTRACT

New compounds of the nitrofuran series are provided, having the following general base formula:

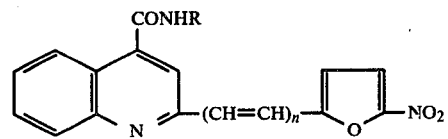

where
R = CH$_2$CH$_2$CH$_2$OH; —CH(CH$_3$)(CH$_2$)$_3$N(C$_2$H$_5$)$_2$
n = 1,2 and which may be in the form of salts.

These compounds, both in the form of base and salt, exhibit a contact-action antiblastic effect. The advantage of these compounds resides in high selectivity of their action on tumoral cells combined with a germicidal activity.

These compounds may be used in the medicine as an active source of antiblastic preparations.

3 Claims, No Drawings

SUBSTITUTED 2-[2'-(5''-NITROFURYL-2''')VINYL-AND 4'-(5''-NITROFURYL-2''-1,3-BUTADIERYL]QUINOLINE-4-CARBOXYLIC ACID AMIDES AND SALTS THEREOF

FIELD OF THE INVENTION

The invention relates to new chemical compounds of the nitrofuran series, and more specifically to substituted 2-[2'-(5''-nitrofuryl-2''')vinyl- and 4'-(5''-nitrofuryl-2''')-1,3butadienyl] quinoline-4-carboxylic acid amides and water-soluble salts thereof. These compounds exhibit antiblastic activity.

BACKGROUND OF THE INVENTION

Known in the art are a great number of chemical compounds exhibiting antiblastic activity, including 5-nitrofuran derivatives.

First reports on antitumor activity of compounds of the nitrofuran series are associated with nitrofurazone (furacin) [Green M. N., Firedgood Ch.E.- "Proc. Soc. Exp. Biol. N.Y.; 1948, v. 69, p. 603–604; Vasilieva V. A., Tutkevich L. M.- "Izv. AN. Latv. SSR, 1950, v. 37, pp. 57–64 (in Russian); Tutkevich L. M. - in the book "Furacin and Application Experience" (in Russian). Riga. 1953, pp. 175–180; Prior J. T., Ferguson J. H. - "Cancer (Philad.)". 1950. v. 3. pp. 1062–1072; Friedgood Ch., Green M. N. - "Cancer Res.". "Cancer Res.". 1950, v. 10. pp. 613–615] and with nitrofurfurylidene propane dinitryl [Petrakis N. L., Bierman H. R., Shimkin M. B.-"Cancer Res.". 1952. v. 12. p. 573; Gal E. M., Creenberg D. M.- "J. Am. Chem. Soc.". 1951. v. 73. pp. 502–503]. Later on, nitrofurazone was used for treating testicular tumors, mainly seminoma and its metastases [Friedgood Ch. E., Danza A. L., Boccabella A.- "Cancer Res." 1952. v. 12. pp. 262–263; Wildermuth O.- "Radiology". 1955. v. 65. pp. 599–603; I. Shiyama K. G., Adachi J- "Cancer Chemother. Abstr."1964. v. 5. pp. 439–440; Karol H. J.-"J. Urol (Baltimore)". 1960. v. 84. pp. 120–122; Hayllar B. L., O'Neal A. H. Dotterer J. A.- "J. Urol (Baltimore),". 1960. v. 84. pp. 565–568]. The data of clinical observations have given scientists an impetus to search for new nitrofuran derivatives exhibiting a stronger antitumor acitivity and less pronounced toxicity, and to study the role of various substitutes in the molecule of such compounds in antitumor activity thereof [Saidela F., Roye R., Bizany E. et al.- "Proceedings of the 8th International Anticancer Congress". v. 6.M., 1962, pp. 119–121].

During investigations into antitumor activity of nitrofuran derivatives it has been found that 5-nitrofuran decelerates the growth of Jensen sarcoma and Walker carcinosarcoma by 39–51%. 5-nitrofurfural, its vinylogs and acetals exhibit about the same activity and a higher acute toxicity. An antiblastic effect is caused by products of condensation of aldehydes of the nitrofuran series with (β-hydrazinoethyl)pyridine, 3-hydrazino-4-amino-1,2,4-triazole [Giller S. A., Kalnberga R. Yu., Zidermane A. A. et al. In the book "Methods of Synthesis and Search for Antitumor Preparations" (in Russian). Iss. 2. M. 1967. pp. 75–81; Giller S. A. et al. In the book "Furozolidine". (in Russian). Riga, 1962. pp. 5–18; Duavarte A. Zh., Zidermane A. A., Kravchenko I. M. et al. In the book "Proceedings of the 1st All-Union Conference on Chemotherapy of Malignant Tumors." Riga. 1968. pp. 216–217; Duavarte A. Zh. et al. In the book "Antitumor Compounds of the 5-nitrofuran Series." (in Russian). Riga, 1972. pp. 17–30)] and 5-aminobenzimidazol [Fuska J., Fuskova A., Jurasek A. "Neoplasma (Bratisl.)". 1973. v. 20. pp. 171–179].

In the search for new antitumor preparations nitrofuran derivatives containing alkylating groups, such as N,N-bis (2-chloroethyl)hydrazide, N,N-bis(2-chloroethyl)hydrazine and N,N-bis(2-chloroethyl)amide have been synthesized [Giller S. A. et al. In the book "Methods of Synthesis and Search for Antitumor Preparations" (in Russian). Iss. 2. M., 1967. pp. 75–81; Duavarte A. Zh., Zidermane A. A. et al. In the book "Proceedings of the 1st All-Union Conference on Chemotherapy of Malignant Tumors" (in Russian). Riga. 1968. pp. 264–265; 266; Duavarte A. Zh. In the book "Antitumor Compounds of the 5-nitrofuran Series." (in Russian). Riga. 1972. pp. 33–44]. Beginning with 1964, synthesis and studies of biological properties of nitrofurylpolyenyl heterocycles were conducted, that is compounds of a new structural type were studies, and the positive result was due to a combination of nitrofuran and heterocycle in one molecule by using a system of —CH═CH— bonds (USSR Inventor's Certificate No. 333835). Nitrofurylvinyl pyrimidines are most active among the compounds of this vlass Katae H., Iwana H., Takase Y. et al.- "Arzneimittel-Forsch.", 1967, Bd. 17.s. 1030–1034; Kravchanko I. M. Zidermane A. A. et al. in the book "Proceedings of the 1st All-Union Conference on Chemotherapy of Malignant Tumors. Riga". 1968. pp. 234–235 and also quinolines Zidermane A. A. et al. "Fharmacology and Toxicology". 1970. No. 6. pp. 711–715; Miura K., Ikeda M., Oohashi T. et al. - "J. pharm. Soc. Jap.". 1964. v. 84. pp. 341–345; Ujiie T.- "Chem. pharm. Bull." 1966. v. 14. pp. 461–466; Miura K. et al. - "J. pharm. Soc. Jap.". 1964. v. 84. pp. 537–543; Miura K., Okda I. "Chem. pharm. Bull.". 1965. v. 13, pp. 525–528.

A known 2-[2'-(5''-nitrofuryl-2''')vinyl]quinoline-4-carboxylic acid amide prepared by condensation reaction of 2-methyl-quinoline-4-carboxylic acid amide with 5-nitrofurfural exhibits a very narrow range of antitumoral activity [K. Miura, M. Ikeda, T. Oohashi, Y. Igarashi. "J. Pharm. Soc. Japan." 1964, 84(6). pp. 537–543; K. Miura, I. Okada. "Chem. Pharm. Bull." 1965. 13 (15). pp. 525–528]. We have not found any antitumor activity for Jensen sarcoma, Pliss lymphosarcoma and Walker carcinosarcoma with peroral administration of 2-[2'-(5''-nitrofuryl-2''')vinyl] quinoline-4-carboxylic acid amide.

As far as the biochemical mechanism of antitumoral activity of non-alkylating 5-nitrofurans is concerned, including nitrofurylvinyl- and nitrofurylbutadiene quinolines, we have found that these compounds decelerate respiration associated with phosphorylation, and some nitrofurylvinyl quinolines inhibit the activity of dehydrogeneses of ascitic cells of Ehrlich tumor, biosynthesis of DNA, RNA and proteins.

All above-described 5-nitrofuran derivatives have not found any practical application in the medicine so far in view of toxicity, low selectivity of antiblastic activity and poor solubility.

SUMMARY OF THE INVENTION

It is an object of the invention to extend the range of chemotherapeutic preparations selectivity acting on malignant tumors and exhibiting less pronounced toxicity.

According to the invention, there are provided new substituted 2-[2''-(5''-nitrofuryl-2'')vinyl- and 4-(5''-nitrofuryl-2'')-1,3-butadienyl] quinoline-4-carboxylic acid amides (base) of formula I:

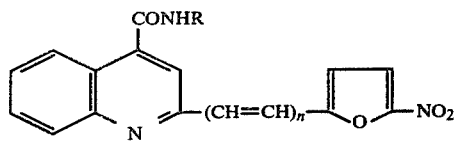

wherein
R = —CH$_2$CH$_2$CH$_2$OH;
—CH(CH$_3$)(CH$_2$)$_3$N(C$_2$H$_5$)$_2$
n = 1,2
or salts thereof of formula II:

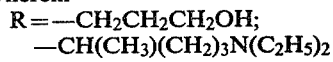

wherein
R = —CH$_2$CH$_2$CH$_2$OH;
—CH(CH$_3$)(CH$_2$)$_3$N(C$_2$H$_5$)$_2$
n = 1,2, K = acid We have found that these substances exhibit a clearly marked antiblastic activity and selective contact action on tumor cell.

DETAILED DESCRIPTION OF THE INVENTION

Figure 1:
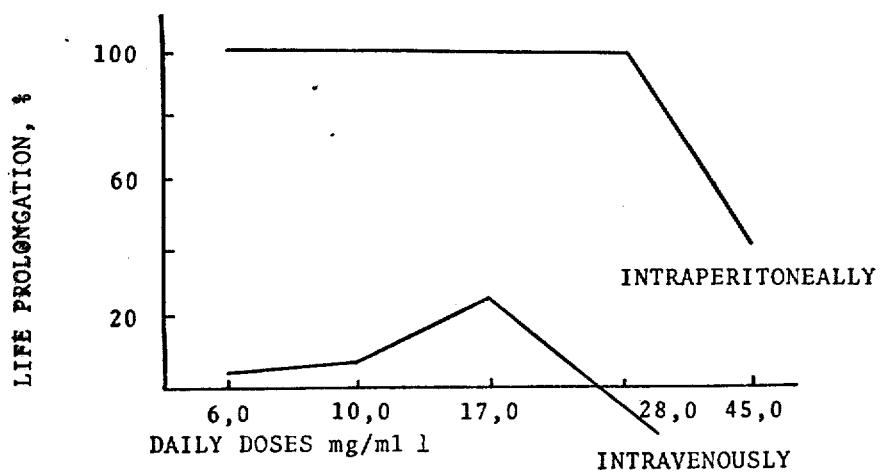

Substituted 2-[2'-(5''-nitrofuryl-2'')vinyl-and 4'-(5''-nitrofuryl-2'')-1,3-butadienyl] quinoline-4-carboxylic acid amides of the above formula (I) are prepared by reacting 2-[2'-(5''-nitrofuryl-2'')vinyl- or 4'-(5''-nitrofuryl-2'')-1,3-butadienyl] quinoline-4-carboxylic acids with thionyl chloride, with subsequent treatment of the isolated 2-[2'-(5''-nitrofuryl-2'')vinyl- and 4'-(5''-nitrofuryl-2'')-1,3-butadienyl] quinoline-4-carboxylic acid chloride hydrochlorides with amines RNH$_2$, wherein
R = —CH$_2$CH$_2$CH$_2$OH or —CH(CH$_3$)(CH$_2$)$_3$N(C$_2$H$_5$)$_2$.

The reaction of said acid chlorides and said amine may occur in stoichiometric amounts or with an excess of said amine in an aqueous medium. In case the reaction involves stoichiometric amounts, it is preferably conducted in the presence of triethylamine. Salts of the above-mentioned compounds may be prepared by reaction with acids, e.g. with ortho-phosphoric acid, hydrochloric acid or hydrobromic acid.

The reaction occurs in accordance with the following scheme:

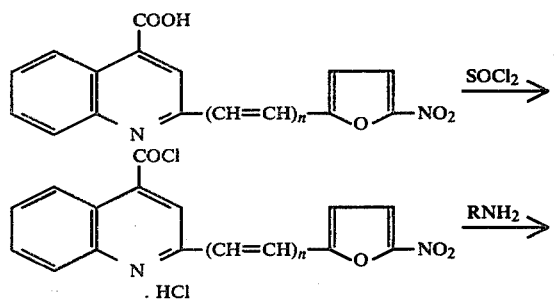

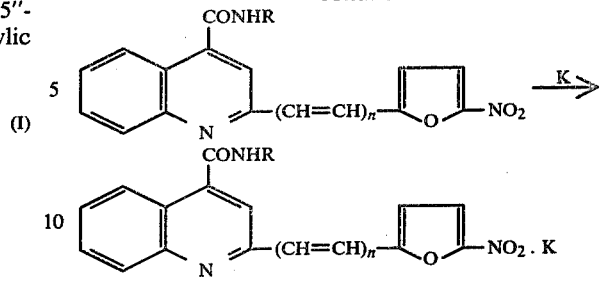

wherein R = —CH$_2$CH$_2$CH$_2$OH, —CH(CH$_3$)(CH$_2$)$_3$N(C$_2$H$_5$)$_2$; n = 1,2; K is acid.

The resultant substances are in the form of crystalline powder of yellow to orange colour; the bases are poorly soluble in water, readily soluble in organic solvents, whereas their salts are readily soluble in water.

Starting 2-[2'-(5''-nitrofuryl-2'')vinyl- and 4'-(5''-nitrofuryl-2'')-1,3-butadienyl] qunioline 4-carboxylic acids are known and readily available substances.

Substituted 2-[2'-(5''-nitrofuryl-2'')vinyl- and 4'-(5''-nitrofuryl-2'')-1,3-butadienyl] quinoline-4-carboxylic acid amides and salts thereof exhibit a marked antiblastic activity in respect of Ehrlich ascitic carcinoma, sarcoma 37, lymphatic leukemia L 5178 and an antimetastatic activity in respect of Lewis lung carcinoma and Walker carcinosarcoma. A certain antitumor effect was observed in respect of sarcomas 180, AK, mammary gland adenocarcinoma AK 755, large intestine adenocarcinoma acatol-1, melanoma B16 and La hemocytoblastosis.

As regards their antitumor activity, these compounds are as good as and, in respect of Ehrlich ascitic tumor, even better than such well known antitumor preparations as thioguanine, cyclocytidine and cyclophosphane (as increase in mice life is 100,138 and 0%, respectively). Moreover, the class of compounds according to the invention differs from the prior art preparations both in structure and mechanism of antitumoral activity.

During the study of the antitumoral activity of the compounds it has been found that:

2-[2'-(5''-nitrofuryl-2'')vinyl] quinoline-4-carboxylic acid (γ-hydroxypropyl) amide prolongs the life of mice with Ehrlich ascitic tumor by up to 120% in doses of from 7.5 mg/kg to 12.5 mg/kg with five injections; with sarcoma 37 the respective figure is 90% with a dose of 12.5 mg/kg.

The life of mice with sarcoma AK was prolonged by up to 20% with a dose of 2.8 mg/kg and with lymphatic leukemia L 5178 by up to 40%.

2-[4'-(5''-nitrofuryl-2'')-1,3-butadienyl] quinoline-4-carboxylic acid (γ-hydroxypropyl) amide prolongs the life of mice with Ehrlich ascitic tumor by up to 80% in a dose of 17 mg/kg, with Lymphatic leukemia L 5178 by up to 40% in a dose of 1 mg/kg and by about 20% with acatol-1 and La hemocytoblastosis in a dose of 10 mg/kg.

2-[2'-(5''-nitrofuryl-2'') vinyl] quinoline-4-carboxylic acid α-methyl-δ-diethylaminobutyl) amide prolongs the life of mice with Ehrlich ascitic tumor by from 70 to 130% with three injections in doses of 10 and 17 mg/kg; by from 30 to 140% with lymphatic leukemia L 5178 in a dose of 6 to 28 mg/kg; by up to 25% with melanoma B16 in a dose of 17 mg/kg and by up to 20% with sarcomas 180 and AK.

When this compound was studied as applied to metastic animals, the life of mice with Lewis lung carcinoma was prolonged by 30% with daily doses of 6 and 10 mg/kg.

[2-(2'(5''-nitrofuryl-2'')vinyl] quinoline-4-carboxylic acid γ-methyl- δ-diethylaminobutyl)amide diphosphate prolongs the life of mice with Ehrlich ascitic tumor with 3-5 intraperitoneal injections with daily doses from 10 to 28 mg/kg by from 140 to 180%, and in case of lymphatic leukemia by up to 130%.

Prolongation of life of mice was observed with adenocarcinoma 755 and sarcoma 180 by up to 20% with daily doses of 10 and 17 mg/kg.

Large intestine adenocarcinoma acatol-1 is sensitive to these compounds.

During the studies of metastases it has been observed that the compounds given in a daily dose of 3.6 mg/kg prolonged the life of rats with Walker carcinoma by 75%.

2-[4'-(5''-Nitrofuryl-2'')-1,3-butadienyl] quinoline 4-carboxylic acid (α-methyl-δ-diethylaminobutyl) amide di- and triphosphate prolong the life of mice with sarcoma 37 by up to 120% in a daily dose of 17 mg/kg with intraperitoneal injection; by from 60 to 160% in doses of 3.6-10 mg/kg with Ehrlich ascitic tumor. Sarcoma 180, large intestine adenocarcinoma acatol-1 and lymphatic leukemia L 5178 exhibit a certain sensitivity to this preparation.

2-[2'-(5''-nitrofuryl-2'')vinyl] quinoline-4-carboxylic acid (α-methyl-δ-diethylaminobutyl) amide chloride prolongs the life of mice with Ehrlich ascitic tumor with a single intraperitoneal injection in a dose of 6 mg/kg by 85% (the injection of the preparation was made 7 days after the tumor was inoculated).

2-[2'-(5''-nitrofuryl-2'')vinyl] quinoline-4-carboxylic acid (α-methyl-δ-diethylaminobutyl)amide bromide prolongs the life of mice with Ehrlich ascitic tumor with a single intraperitoneal injection in a dose of 28 mg/kg by 85% (the preparation was injected 7 days after the tumor was inoculated).

A particular attention is drawn to the compound 2-[2'-(5''-nitrofuryl-2'')vinyl] quinoline-4-carboxylic acid (α-methyl-δ-diethylaminobutyl)amide triphosphate having the structure corresponding to the above-given formula II, wherein $R=-CH(CH_3)(CH_2)_3N(C_2H_5)_2$; $n=1$; $K=3H_3PO_4$.

This compound was used in the form of aqueous solutions, The preparation containing this compound in an aqueous solution as an active source was conventionally named giniguine.

An important advantage of the preparation giniquine resides in its selective action on tumor cells.

The preparation giniquine will be described in detail below.

The results of the study of the cytostatics according to the invention in the series of nitrofurylvinyl-and nitrofurylbutadienyl quinolines show that the new antitumor preparation exhibiting a contact action-giniquine may prove useful for the treatment of patients suffering from carcinomatose exudate in pleural and abdominal cavities.

It is known that an intensive accumulation of exudate in serous cavities requires repeated punctures. A bacterial infection may, however, develop upon such interferences in case of exudate. Therefore, antitumor preparations exhibiting a germicidal activity, in addition to the antitumor activity, deserve a particular attention.

We have found that giniquine combines in itself both actions.

Still another advantage of giniquine resides in the absence of an inhibiting influences on wound healing processes.

In an experiment, a contact antitumor action of giniquine was revealed in respect of Ehrlich ascitic tumor. The experiment was conducted as follows. $10^6$ cells of Erlich tumuor were injected in common white mice intraperitoneally, the dose being given per each animal. Giniquine was injected intraperitonealy 1,5 and 9 days after the tumor was implanted, in five different doses (6,10,17,28 and 45 mg/kg). Each dose of the preparation was tested in six mice. The control group included 18 mice. Giniquine solution was prepared by dissolving the substance ex tempore in distilled water or in a buffer. The effect of the preparation is shown on charts 1,2,3.

Giniquine was tested in various concentractions from 0.1 to 0.35% solution. It has been found that the antitumoral effect of giniquine did not change within this range of concentrations.

The results of tests on the antitumor activity of giniquine are illustrated in the accompanying drawings which comprise three charts containing the data described below:

From the data given in Chart 1 it can be seen that giniquine mainly exhibits a contact antitumor activity since the life of test mice was prolonged by 100% with intraperitoneal injection and only by 25% with intravenous injection.

It is interesting to note that the antitumor effect of giniquine is the same both with a single intraperitoneal injection on the first day after the implantation of tumor and with five injections at 1,2,3,4,7 days after the implantation of tumor (Chart 2).

Substantial antitumor effect of giniquine was also observed with deferred intraperitoneal injection (on the 7th day after the implantation of tumor (Chart 3). With giniquine injection on the first day after implantation, life of test mice was prolonged by 90%, on the third day-by 80%, on the 7th day-by 100%, on the 14th day-by 55%. Therefore the antitumor activity of giniquine may be high enough even with a large number of tumor cells being formed.

Apart from the tests on Ehrlich ascitic tumor, giniquine was studied on twelve more inoculated tumors. Seven tumors (melanoma B16, sarcoma AK, large intestine carcinoma acatol-1, sarcoma 180, adenocarcinoma 755, Lewis lung carcinoma and sarcoma 37) were inoculated subcutaneously with 50 mg of tumoral cells per mouse. Four tumors (lymphatic leukemies L 5178, L 5178Y, L 1210 and P-388) were inoculated intraperitoneally with $10^6$ cells per mouse. One tumor (La, hemocytoblastosis) was inoculated intraperitoneally by injecting 50 mg of cell suspension of spleen and liver of mice suffering La hemocytoblastosis, per mouse. Giniquine was injected intraperitoneally five times for seven days: 1,2,3,4,7 days or 3,4,5,6,7 days after the implantation of tumor. The rate of deceleration of the tumor growth was established 14 days after the ultimate injection of giniquine; life of test animals was recorded for 60 days.

It has been found that giniquine had a slight antitumor effect on melanoma B16, sarcoma AK, acatol-1, sarcoma 180, adenocarcinoma 755 and lymphatic leukemia L 5178 (see Tables 1 and 2).

Lymphatic leukemies L-5178Y, L-1210 and P-388, La hemocytoblastosis, Lewis lung carcinoma and sarcoma 37 are practically insensitive to giniquine.

In some experiments the influence of the known preparation fluorofur on the antitumoral activity of giniquine was studied. It has been found that in some cases fluorafur can cause adding up and, in a number of instances, potentiation of antitumor effect of giniquine. The tests were made on Ehrlich ascitic tumor. The preparations were injected 1,2,3,4 and 7 days after the implantation of tumor. Giniquine was injected intraperitoneally and fluorafur-subcutaneously.

The results suggest that in patients with tumors sensitive to antiblastic acitivity of fluorafur, (intracavitary) injection of giniquine may be combined with intravenous injection or peroral administration of fluorafur. The data are given in Table 3.

It can be seen from Table 4 that mice sensitivity to giniquine does not depend on the sex of test mice. It should be noted that with a single intraperitoneal injection of the preparation in mice 7 days after the implantation of Ehrlich ascitic tumor toxicity of giniquine is three times lower. With intravenous injection, the giniquine toxicity is five times greater compared to the intraperitoneal injection. With peroral administration, toxicity of giniquine is 4-5 times lower.

The biological availability of giniquine was studied on common white male rats with a mass of 150-200 g and common white male mice with a mass of 25-30 g. The test began seven days after Ehrlich ascitic carcinoma was inoculated to the animals.

Giniquine was injected intraperitoneally in 100 mg/kg doses, using distilled water as a solvent. The animals were slaughtered at preset time intervals (5,15,30 and 60 minutes) and a biological material (blood and liver for rats and ascites for mice) was taken for analysis. To separate ascitic fluid from the tumor cells, ascites was centrifuged at 2000 r.p.m. for 10 minutes. The precipitate was washed with a mixture of physiological solution and heparin and was again centrifuged under the same conditions, 20% homogenates in distilled water were prepared from ascitic cells.

Table 1

ANTITUMORAL ACTIVITY OF GINIQUINE

| Test System | Mice | Sex | Injection method | Injection timing | Daily doses | Optim. daily dose mg/kg | Deceleration of tumor growth, % | Optim. daily dose, mg/kg | Max. prolongation of life, % |
|---|---|---|---|---|---|---|---|---|---|
| 1 | 2 | 3 | 4 | 5 | 6 | 7 | 8 | 9 | 10 |
| Melanoma B16 | BDF$_1$ | ♂ | Intraperitoneal | 1,2,5, 6,7 days | 2.2-17.0 | 17.0 | 48 | 17.0 | 10 |
| Sarcoma AK | common | ♀ | Intraperitoneal | 3,4,5, 6,7 days | " | 2.2 | 46 | 10.0 | 15 |
| Acatol-1 | BALB/c | ♀ | Intraperitoneal | 3,4,5, 6,7 days | " | 10.0 | 38 | 10.0 | 25 |
| Sarcoma 180 | common | ♀ | Intraperitoneal | 3,4,5, 6,7 days | " | 6.0 | 37 | 10.0 | 23 |
| Adenocarcinoma 755 | BDF$_1$ | ♀ | Intraperitoneal | 1,2,3, 4,7 days | " | 6.0 | 28 | 6.0 | 25 |

Table 2

ANTITUMOR ACTIVITY OF GINIQUINE

| Test system | Mice | Sex | Injection method | Injection timing | Daily doses, mg/kg | Optimum daily dose, mg/kg | Max. life prolong. % |
|---|---|---|---|---|---|---|---|
| Lymphatic leukemia L 5178 | common | ♀ | Intraperitoneal | 1,2,3,4,7 days | 3.6-17.0 | 10.0 | 30 |
| Lymphatic leukemia L 5178Y | BDF$_1$ | ♀ | Intraperitoneal | " | " | 6.0 | 5 |
| Lymphatic leukemia L-1210 | BDF$_1$ | ♂ | Intraperitoneal | " | 6.0-28.0 | 6. | 15 |
| Lymphatic leukemia B-388 | BDF$_1$ | ♀ | Intraperitoneal | " | 3.6-17.0 | 10.0 | 12 |
| La hemocytoblastosis | C$_{57}$BL/6Y | ♀ | Intraperitoneal | " | " | 10.0 | 5 |
| Lewis lung carcinoma | BDF$_1$ | ♀ | Intraperitoneal | " | 2.1-45.0 | 6.0 | 15 |
| Sarcoma 37 | common | ♀ | Intraperitoneal | " | 6.0-28.0 | 0 | 0 |

Table 3

Influence of fluorafur on antitumor activity of giniquine with their injection 1,2,3,4,7 days after intraperitoneal implantation of Ehrlich ascitic tumor

| Test No. | Giniquine Daily dose, mg/kg | Giniquine Lite prolongation % | Fluorafur Daily dose, mg/kg | Fluorafur Life prolongation, % | Giniquine+fluorafur Daily dose, mg/kg | Giniquine+fluorafur Life prolongation, % |
|---|---|---|---|---|---|---|
| 1 | 3.6 | 55 | 39.0 | 35 | 1.8 + 20.0 | 89 |
|  | 6.0 | 67 | 65.0 | 37 | 3.0 + 33.0 | 100 |
|  | 10.0 | 38 | 108.0 | 40 | 5.0 + 54.0 | 100 |
|  | 17.0 | −5 | 180.0 | 52 | 8.5 + 90.0 | 102 |
| 2 | 3.6 | 45 | 39.0 | 18 | 1.8 + 20.0 | 57 |
|  | 6.0 | 98 | 65.0 | −5 | 3.0 + 33.0 | 65 |
|  | 10.0 | 5 | 108.0 | −17 | 5.0 + 54.0 | 143 |
|  | 17.0 | −48 | 180.0 | −33 | 8.5 + 90.0 | 13 |

Note:
giniquine was injected intraperitoneally, and fluorafursubcutaneously.

The data on the study of giniquine toxicity are given in Table 4.

Table 4

$LD_{50}$ for giniquine

| Test animals | Application method | Single injection administration ♀ | Single injection administration ♂ | Ten injections ♀ | Ten injections ♂ |
|---|---|---|---|---|---|
| Intact mice | Intraperitoneal injection | 33/25.6 + 42.6/ | 30/22.4–40.2/ | 8/6.06–10.56/ | 7.3/4.8 + 10.9/ |
| Mice with 7-days Erlich ascitic tumor | Intraperitoneal injection | 99/87.6–111.9/ | — | 10/8.3–12.0/ | 7.0/4.9 + 10.5/ |
| Mice with 7-days Erlich ascitic tumor | Intravenously injection | 17.5/14.2–21.5/ | 20/13.3–30.0/ | — | — |
| Mice with 7-days Erlich ascitic tumor | Peroral administration | 360/226–576/ | 500/333–750/ | — | — |

Giniquine was extracted from the biological material with chloroform. In the in vitro tests it was found that extraction with chloroform permits the 100% yield of the preparation to be achieved from the biological material.

The extraction procedure comprised the following stages: 0.1 ml of ethyl alcohol were added to 1 ml of tested sample and the solution was thoroughly mixed with 0.5 ml of a saturated potassium carbonate solution, then 4 ml of chloroform was added. Closed test tubes were vigorously shaken on a rocker for one hour. After the shaking, the samples were centrifuged at 5000 r.p.m. for ten minutes. The chloroform layer was used for analysis. Daylight was avoided.

Concentration of the preparation in biological samples was determined by spectrophotometry at 400 nm using molar absorption factor ($\epsilon 0.10^{-3} = 36.04$).

The results were expressed in $\mu g/ml$ of sample. Minimum sensitivity of the method was 1.1 $\mu g/ml$.

The study of the biological availability of giniquine with intraperitoneal injection showed that as early as in five minutes the preparation can be discovered in blood, which attested to its rapid penetration through tissue barriers. The maximum level of giniquine was observed 30 minutes after the injection and was 23 $\mu g/ml$. Subsequently the content of the preparation in the blood serum rapidly decreased and was 3 $\mu g/ml$ at the end of the tests (60 minutes), which approximates the sensitivity limit of the method. Rapid disappearance of the preparation from the blood is likely to be due both to its propagation among tissues and organs and removal from the body.

It has been found that giniquine accumulates in the liver in concentrations slightly above concentration in blood (maximum concentration measured 20 minutes after the injection was 28 $\mu g/ml$).

The concentration of giniquine after its intraperitoneal injection is much greater in ascitic cells as compared to the ascitic fluid. The maximum concentration of the preparation in cells, which was observed at the earliest intervals after the sampling (five minutes), was four times greater than that in the ascitic fluid (40 and 10 $\mu g/ml$, respectively), which was indicative of its bond with cellular components. At the end of the observation period (60 minutes) concentration of giniquine in tumoral cells was also greater than that in ascitic fluid.

The data on prevailing accumulation of giniquine in ascitic cells permit the preparation to be recommended as a contact-action one.

It is known that cytoscopic action of the majority of antitumor preparations is associated with suppression of biosynthesis of macromolecules. Consequently, the efficiency of inhibition of biosynthesis of macromolecules with chemotherapeutical preparations in tumoral and normal tissues may be used as an index of selectivity of their action, which mainly determines their suitability for oncological practice.

The effect of giniquine on biosynthesis of molecules in the in vitro tests was studied with suspensions of cells of Ehrlich ascitic tumor. The tests were conducted with common white mice of a mass of 18-20 g. Ascites was taken 7-8 days after the inoculation, dissolved with a cool Eagle medium (pH 7.4) containing 0.1% of heparin, and the cells were precipitated by centrifuging at 600 g. The cells were washed twice with the same medium, and a 10% suspension of the cells in the Eagle medium was prepared.

The effect of giniquine on biosynthesis of DNA, RNA and protein in the cells of Ehrlich ascitic tumor was assessed on the basis of incorporation of cells of specific labeled precursors into acid-insoluble fraction: $2\text{-}^{14}C$-thymidine, $2\text{-}^{14}C$-uridine and $2\text{-}^{14}C$-leucine, respectively.

The incubating medium contained, in a total volume of 2 ml, 100 mg of tumoral cells in the form of suspension, Eagle medium (pH 7.4), giniquine in a concentration of $1.10^{-4}$m and labeled precursors of nucleic acids and protein with a radioactivity corresponding to 0.1 $\mu c$. Control samples contained a corresponding volume of distilled water to replace the preparation solution.

The incubation was conducted in Warburg apparatus vessels at 37° C. for one hour. After the incubation, tumoral cells were fixed by adding cool 10% trichloracetic acid to the incubating medium (1:1). Concurrently a control sample without incubation was prepared, to which, before adding the cell suspension, was added 10% trichloracetic acid in the same ratio.

The precipitated cells were extracted for 20 minutes at 0° C. with 5% trichloroacetic acid. The samples were then filtered through millipore filters (HUFS, pore diameter 0.4 $\mu$). The precipitate on the filter was washed twice with 5 ml of cool 5% trichloracetic acid and once with 5 ml of toluene. The filters were dried in the air and transferred into quartz flasks containing 10 ml of toluene scintillator. The radioactivity was determined by means of a liquid scintillation counter. The results were expressed in percent of the control.

The influence of giniquine on biosynthetic processes in the in vivo tests was studied on common white mice of a mass of 25-35 g with Ehrlich ascitic tumor.

The mice were divided into two groups. The animals in the first group were given a single injection of the preparation in differing doses, and the animals in the second group were treated with distilled water. Three series of experiments were conducted. In the first series of tests (16 mice) the preparation was injected in a dose of 100 mg/kg (suboptimal dose), and the animals were decapitated one hour after the injection; in the second test series (16 mice) the animals were slaughtered 3 hours after the injection with other conditions being the same. In the third test series (35 mice) the influence of giniquine on plastic metabolism in tumor cells and normal tissues was studied 24 hours after the injection of a 0.33% solution of the preparation in a dose of 28 mg/kg (therapeutical dose).

Labeled precursors of nucleic acids and protein were injected intraperitoneally one hour before the slaughter of the animals (50 $\mu c$/100 g). Ascitic fluid, as well as liver and spleen, mucous membrane of small intestine, brain, kidneys and lungs were taken for analysis. 10% suspension was prepared from tumor cells, and 10% homogenates were prepared from tissues in a physiological solution.

Tumor cells and tissue homogenates for precipitation of nucleic acids were treated with 57% perchloric acid (10:1). Acid-soluble fraction was removed by washing the precipitate twice with 5 ml of 5% perchloic acid with subsequent centrifuging at 2000 g. Nucleic acids were hydrolyzed by the Schneider method. Radioactivity of DNA and RNA fractions was measured by means of a liquid scintillation counter. The quantity of DNA and RNA was determined by spectrophotometry: the quantity of DNA was determined with diphenylamine, and RNA- with orcin.

To prepare protein hydrolysate, the suspension of tumoral cells and homogenates of normal tissues were treated with cool 10% trichloracetic acid (1:4), with subsequent centrifuging at 2000 g for ten minutes. The precipitate was washed twice with 5 ml of 10% trichloracetic acid. Lipoids were removed by a consecutive treatment of the precipitate with ethanol, saturated solution of sodium acetate, a mixture of ethanol and ether (3:1) and ether. To prepare protein hyhdrolysate, 4 ml of 0.3N KOH were added to the precipitate, and the mixture was placed into a thermostatic chamber at 37° C. for 60 minutes. The radioactivity was measured by means of a liquid scintillation counter. Protein was quantitatively determined by spectrophotometry using a microbiuret reaction.

The data of in vitro tests for the studies of the influence of giniquine on the incorporation of labeled precursors of giniquine on the incorporation of labeled precursors of DNA, RNA and protein in acid-insoluble fraction of cells of Ehrlich ascitic tumor are given in Table 5.

Table 5

Effect of giniquine on the incorporation of $2\text{-}^{14}C$-thymidine, $2\text{-}^{14}C$-uridine and $2\text{-}^{14}C$-leucine in acid-insoluble fraction of cells of Ehrlich ascitic tumor cells

| Radioactive precursor | Giniquine concentration, M | Incorporation in percent of control |
|---|---|---|
| $2\text{-}^{14}C$-thymidine | $1.10^{-4}$ | 61.0 |
| $2\text{-}^{14}C$-uridine | " | 52.0 |
| $2\text{-}^{14}C$-leucine | " | 86.0 |

It will be apparent from the Table that under the action of giniquine in a concentration of $1.10^{-4}$ M the incorporation of labeled precursors of DNA, RNA and protein in acid-insoluble fraction of cells of Ehrlich ascitic tumor is disturbed compared to the control. As giniquine is designed for contact administration in the form of 0.33% solution, it was to study the effect of the preparation on tumor cells using this particular concentration which is about 50 times the concentration employed in the biochemical tests in vitro ($1.10^{-4}$ M corresponds to 0.007%), as well as the concentration which is three times lower than the proposed concentration (0.1%). The results of in vitro experiments study of the effect of 0.3 and 0.1% solutions of giniquine on the incorporation of $2\text{-}^{14}C$-thymidine in the acid-insoluble fraction (DNA) of Erlich cells are presented in Table 6.

Table 6

Effect of Giniquine on the incorporation of $2\text{-}^{14}C$-thymidine in DNA of cells of Ehrlich ascitic tumor

| Concentration | Incorporation in % of control |
|---|---|
| 0.1 | 2.4 |
| 0.3 | 0.7 |

The above results show that with a contact injection of 0.3% solution of giniquine practically complete suppression of biosynthesis of DNA in tumor cells occurs. This concentration is not likely to be reduced since in the presence of 0.1% of giniquine the synthesis of DNA in tumor cells is still 2.4% of control.

After the fact of decelerating effect of giniquine on biosynthesis in vitro has been established, it appeared to be interesting to reveal what is the influence of the preparation on tumoral cells and normal tissues in vivo. For that purpose, we studied biosynthesis of macromolecules with a short-time action of giniquine (one and three hours) in a suboptimal dose (100 mg/kg) and with a long-term action of the preparation (24 hours) in a therapeutical dose (28 mg/kg).

The results of the tests for studies on the effect of giniquine on biosynthesis of DNA and protein in cells of Ehrlich ascitic tumor, liver and spleen of tumor-carrier mice one and three hours after the injection are given in Tables 7 and 8, respectively.

Table 7

Effect of giniquine on the incorporation of 2-$^{14}$C-thymidine in DNA of tumor cells, liver and spleen of mice with Ehrlich ascitic tumor one and three hours after intraperitoneal injection of the preparation in 100 mg/kg dose

| Biological material | Incorporaion of 2-$^{14}$C-thymidine in DNA in % of control | |
|---|---|---|
| | 1h | 3 h |
| Tumor cells | 43.0 | 30.0 |
| Liver | 106.0 | 93.0 |
| Spleen | 120.0 | 116.0 |

Table 8

Effect of giniquine on the incorporation of 2-$^{14}$C-leucine in protein of tumor cells, liver and spleen of mice with Ehrlich ascitic tumor one and three hours after intraperitoneal injection of the preparation in 100 mg/kg dose

| Biological material | Incorporation of 2-$^{14}$C-leucine in protein in % of control | |
|---|---|---|
| | 1 h | 3 h |
| Tumor cells | 59.0 | 14.0 |
| Liver | 127.0 | 96.0 |
| Spleen | 97.0 | 40.0 |

The tests show that one hour after the injection of the preparation an inhibition of biosynthesis of DNA in tumor cells (57%) occurs, and in normal tissues a certain stimulation of biosynthesis of DNA occurs (by 6% in liver and by 20% in spleen). Three hours after the injection the inhibition in tumor cells increases to reach 70%. A slight inhibition is also observed in the liver (7%), and a stimulation in the spleen amounts to 16%.

The following data were obtained as regards the effect of giniquine on biosynthesis of protein with the above-described injection conditions. One hour after the injection of the preparation biosynthesis of protein was substantially suppressed (41%). In normal tissues- the liver and spleen - the inhibition was not observed or inappreciable. Further investigations showed that three hours after the injection inhibition of biosynthesis of protein in tumor cells was considerably stronger (86%) than in normal tissues (liver -4% and spleen-60%).

On the basis of the above the conclusion may be drawn that maximum inhibition of biosynthesis of protein and DNA occurs in tumor cells, which attests to selectivity of the preparation. This fact, as well as a rapid action of the preparation (one hour after the injection) permits it to be recommended as an antiblastic contact-action preparation.

The results of the tests conducted to study the effect of giniquine on biosynthesis of DNA, RNA and protein 24 hours after the injection of a therapeutical dose of the preparation are given in Table 9.

Table 9

Effect of giniquine on biosynthesis of DNA, RNA and protein in carcinomatous cells and normal tissues of mice with Ehrlich ascitic tumor 24 hours after the intraperitoneal injection of the preparation in 28 mg/kg dose

| Biological material | Incorporation of specific precursors in % of control | | |
|---|---|---|---|
| | DNA | RNA | Protein |
| Tumor cells | 18.0 | 58.0 | 54.0 |
| Mucous membrane of small intestine | 386.0 | 158.0 | 122.0 |
| Liver | 190.0 | 124.0 | 112.0 |
| Spleen | 330.0 | 162.0 | 93.0 |
| Brain | 125.0 | 124.0 | 105.0 |
| Kidneys | 178.0 | 148.0 | 105.0 |
| Lungs | 255.0 | 124.0 | 102.0 |

The data given in table 9 attest to the fact that 24 hours after the injection of giniquine, similarly to the above-described tests, a substantial deceleration of synthesis of macromolecules in tumor cells occurs. Suppression of the incorporation of 2-$^{14}$C-thymidine in DNA is 82%, 2-$^{14}$C-uridine in RNA - 42%, 2-$^{14}$C-leucine in protein −46%. In all normal tissues studied (mucous membrane of small intestine, liver, spleen, brain, kidneys, lungs) a general trend is observed which resides in a stimulation of biosynthesis processes, in particular as far as DNA is concerned.

In view of the above, the conclusion may be drawn that giniquine is a highly active antitumoral preparation exhibiting a contact action. Apart from the antitumoral activity, it also exhibits a germicidal activity. The preparation is efficient enough even with a single injection.

With intraperitoneal injection giniquine mainly accumulates in ascitic cells.

In the in vitro tests giniquine decelerates the incorporation of labeled precursors in DNA, RNA and protein. In the in vivo tests it has the same effect on biosynthesis processes in tumor cells, and in this case a selectivity of its decelerative action on biosynthesis of macromolecules in tumor cells comes to light.

The invention will now be llustrated by examples of the preparaton of substituted 2-[2'-(5''-nitrofuryl-2'')vinyl- and 4-(5''-nitrofuryl-2'')-1,3-butadienyl]quinoline-4-carboxylic acid amides and salts thereof.

EXAMPLE 1

2-[2'-(5''-nitrofuryl-2'')vinyl]quinoline-4-carboxilic acid chloride hydrochloride A mixture of 3.1 g of (0.01 mol.) of 2-[2'-(5''-nitrofuryl-2'')vinyl]quinoline-4-carboxylic acid and 24 g (0.2 mol.) of thionyl chloride was heated under reflux at the boiling point of the mixture for one hour. An excess of thionyl chloride was distilled off under vacuum with a residual pressure of 15 mm Hg, than 10–15 ml of benzene were added, and the distillation-off was repeated to remove traces of thionyl chloride.

The yield of 2-[2'-(5''-nitrofuryl-2'')vinyl]quinoline-4-carboxylic acid chloride hydrochloride was 3.43 g (94% of theory), m.p. 165°–167° C. M.p. after recrystallization 167° C. (benzene).

Analysis %: C-52.61; H 2.56; Cl 19.24; N 7.51; $C_{16}H_{10}N_2O_4Cl_2$. Theory %: C 52.62; H 2.71; Cl 19.41; N 7.67.

The product was sufficiently pure and did not require additional recrystallization.

EXAMPLE 2

2-[4'-(5''-nitrofuryl-2'')-1,3-butadienyl]quinoline-4-carboxylic acid chloride hydrochloride was prepared as described in Example 1 from 2-[4-(5''-nitrofuryl-2'')-1,3-butadienyl]quinoline-4-carboxylic acid and thionyl chloride with the yield of 78%, m.p. 230°–232° C. (with decomposition).

Analysis: C 55.61; H 3.29; N 7.16; Cl 77.92; $C_{18}H_{12}N_2O_4Cl_2$. Theory %: C 55.25; H 3.08; N 7.16; Cl 18.12.

EXAMPLE 3

2-[2'-(5''-nitrofuryl-2'')vinyl]quinoline-4-carboxylic acid (γ-hydroxypropyl)amide.

To a solution of 2.25 g (0.03 mol.) of 1-aminopropanol-3 in 30 ml of water 3.65 g (0.01 mol.) of 2-[2'-(5''-nitrofuryl-2'')vinyl]quinoline-4-carboxylic acid chloride hydrochloride prepared as described in Example 1 were added in small batches with vigorous stirring. The stirring continued for five hours at room temperature, and the mixture was allowed to stay for 12 hours. The resultant precipitate was filtered off, washed with water to obtain a neutral reaction and dried at 90°–100° C. The product was recrystallized from dimethyl formamide. The yield of 2-[2'-(5''-nitrofuryl-2'')vinyl]quinoline-4-carboxylic acid (γ-hydroxypropyl) amide was 3.4 g (98.6%), m.p. 237°–238° C.

Analysis %: C 62.21; H 4.85; N 11.34; $C_{19}H_{17}N_3O_5$. Theory %: C 62.12; H 4.66; N 11.44.

EXAMPLE 4

[4'-(5''-nitrofuryl-2'')-1,3-butadienyl]quinoline-4-carboxylic acid (γ-hydroxypropyl)amide was prepared as described in Example 3 from 1-aminopropanol-3 and 2-[4'-(5''-nitrofuryl-2'')-1,3-butadienyl]quinoline-4-carboxylic acid amide chloride hydrochloride. The yield was 98.3%, m.p. 201°–202° C.

Analysis: C 63.98; H 5.10; N 10.47; $C_{21}H_{19}N_3O_5$. Theory %: C 64.11; H 4.87; N 10.68.

EXAMPLE 5

2-[2'-(5''-nitrofuryl-2'')vinyl]quinoline-4-carboxylic acid (α-methyl-δ-diethylaminobutyl)amide.

3.65 g (0.01 mol.) of 2-[2'-(5''-nitrofuryl-2'')vinyl]quinoline-4-carboxylic acid chloride hydrochloride prepared as described in Example 1 were added in small batches with vigorous stirring to a solution of 4.74 g (0.03 mol.) of diethylamino-4-aminopentane in 50 ml of water. The stirring continued for 6–7 hours, and the reaction mixture was allowed to stay at room temperature for 8–12 hours. The resultant precipitate was filtered off, washed with water to obtain a neutral reaction, dried at 90°–100° C. and recrystallized from dimethyl formamide. The yield of 2-[2'-(5''-nitrofuryl-2'')vinyl]quinoline-4-carboxylic acid (α-methyl-δ-diethylaminobutyl)amide was 3.94 g (87.4%), m.p. 210°–211° C. (with decomposition).

Analysis, %: C 66.42; H 6.58; N 12.69; $C_{25}H_{30}N_4O_4$. Theory, %: C 66.65; H 6.71; N 12.47.

EXAMPLE 6

2-[2'-(5''-nitrofuryl-2'')vinyl]quinoline-4-carboxylic acid (α-methyl-δ-diethylaminobutyl)amide was prepared from 1.58 g (0.01 mol.) of diethylamino-4-aminopentane and 3.65 g (0.01 mol.) of 2-[2'-(5''-nitrofuryl-2'')vinyl]quinoline-4-carboxylic acid chloride hydrochloride in 50 ml of water in the presence of triethylamine. The process was conducted as described in Example 5.

The yield was 3.79 g (84.2% of theory).

EXAMPLE 7

2-[4'-(5''-nitrofuryl-2'')-1,3-butadienyl]quinoline-4-carboxylic acid (α-methyl-δ-diethylaminobutyl)amide.

3.91 g (0.01 mol.) of 2-[4-(5''-nitrofuryl-2'')-1,3-butadienyl]quinoline-4-carboxylic acid chloride hydrochloride were added in small batches to a solution of 1.58 g (0.01 mol.) of diethylamino-4-aminopentane, 8 ml of triethylamine and 50 ml of water with vigorous stirring. The stirring continued for 6–7 hours, and the reaction mixture was allowed to stay at room temperature for 8–12 hours. The resultant precipitate was filtered off, washed with water to obtain a neutral reaction, dried at room temperature at 90°–100° C. and recrystallized from dimethyl formamide. The yield of 2-[4-(5''-nitrofuryl-2'')-1,3-butadienyl]quinoline-4-carboxylic acid (α-methyl-δ-diethylaminobutyl)amide was 3.24 g (68.2%), m.p. 172°–174° C.

Analysis %: C 67.89; H 6.52; N 11.81; $C_{27}H_{32}N_4O_4$. Theory %: C 68.05; H 6.77; N 11.76.

EXAMPLE 8

2-[4'-(5''-nitrofuryl-2'')-1,3-butadienyl]quinoline-4-carboxylic acid (α-methyl-δ-diethylaminobutyl)amide was prepared from 4.74 g (0.03 mol.) of diethylamino-4-aminopentane and 3.91 g (0.01 mol.) of 2-[4-(5''-nitrofuryl-2'')-1,3-butadienyl]quinoline-4-carboxylic acid chloride hydrochloride in 50 ml of water. The process was conducted as described in Example 7.

The yield was 3.36 g (70.7% of theory).

EXAMPLE 9

2-[2'-(5''-nitrofuryl-2'')vinyl]quinoline-4-carboxylic acid (α-methyl-δ-diethylaminobutyl)amide diphosphate.

4.51 g (0.01 mol.) of 2-[2'-(5''-nitrofuryl-2'')vinyl]quinoline-4-carboxylic acid (α-methyl-δ-diethylaminobutyl)amide prepared as described in Examples 5, 6 were dissolved in 2.5–3 l of acetone, 1.5 g of activated carbon were added and the mixture was boiled. The solution was then filtered, cooled, and 2.31 g of 85% ortho-phosphoric acid in 350 ml of acetone were added. The resultant precipitate was filtered off, washed with acetone, dried at 90°–100° C. and recrystallized from an alcohol. The yield of 2-[2'-(5''-nitrofuryl-2'')vinyl]quinoline-4-carboxylic acid (α-methyl-δ-diethylaminobutyl)amide diphosphate was 4.81 g (74.3% of theory), m.p. 180°–181° C.

Analysis, %: C 46.21; H 5.45; N 8.43; P 9.97; $C_{25}H_{30}N_4O_4 \cdot 2H_3PO_4$. Theory, %: C 46.44; H 5.61; N 8.67; P 9.58.

EXAMPLE 10

2-[4'-(5''-nitrofuryl-2'')-1,3-butadienyl]quinoline-4-carboxylic acid (α-methyl-δ-diethylaminobutyl)amide diphosphate was prepared as described in Example 9 from 2-[2'-(5''-nitrofuryl-2'')vinyl]quinoline-4-carboxylic acid (α-methyl-δ-diethylaminobutyl)amide and ortho-phosphoric acid. The yield was 68.1%, m.p. 176°–178° C.

Analysis %: C 47.98; H 5.43; N 8.58; P 9.44; $C_{27}H_{32}N_4O_4.2H_3PO_4$. Theory %: C 48.22; H 5.70; N 8.33; P 9.21.

EXAMPLE 11

2-[2′-(5″-nitrofuryl-2″)vinyl]quinoline-4-carboxylic acid (α-methyl-δ-diethylaminobutyl)amide triphosphate 4.51 g (0.01 mol.) of 2-[2′-(5″-nitrofuryl-2″)vinyl]-quinoline-4-carboxylic acid (α-methyl-δ-diethylaminobutyl)amide prepared as described in Examples 5, 6 were dissolved in 2300 ml of acetone, then 1 g of activated carbon was added, and the mixture was boiled for 10–15 minutes. The solution was then filtered and 3.46 g of 85% ortho-phosphoric acid in 350 ml of acetone were added. If the precipitate was not formed at once, the mixture had to be heated at 50° under an intense stirring for 1–2 minutes. The resultant precipitate was filtered off, washed with acetone and dried at 90°–100° C. The yield of 2-[2′-(5″-nitrofuryl-2″)vinyl]-quinoline-4-carboxylic acid (α-methyl-δ-diethylaminobutyl)amide triphosphate was 7.15 g (96.1%), m.p. 175°–176° C.

Analysis, %: C 40.46; H 5.30; N 7.49; P 12.49; $C_{25}H_{30}N_4O_4.3H_3PO_4$. Theory, %: C 40.33; H 5.28; N 7.53; P 12.48.

EXAMPLE 12

2-[4′-(5″-nitrofuryl-2″)-1,3-butadienyl]quinoline-4-carboxylic acid (α-methyl-δ-diethylaminobutyl)amide triphosphate was prepared as described in Example 11 from 2-[4′-(5″-nitrofuryl-2″)-1,3-butadienyl]quinoline-4-carboxylic acid (α-methyl-δ-diethylaminobutyl)amide and ortho-phosphoric acid. The yield was 74.1%, m.p. 179°–180° C.

Analysis %: C 41.97; H 5.29; N 7.66; P 12.46; $C_{27}H_{32}N_4O_4.3H_3PO_4$. Theory %: C 42.08; H 5.35; N 7.27; P 12.06.

EXAMPLE 13

2-[2′-(5″-nitrofuryl-2″)vinyl]quinoline-4-carboxylic acid (α-methyl-δ-diethylaminobutyl)amide chloride.

4.51 g (0.01 mol.) of 2-[2′-(5″-nitrofuryl-2″)vinyl]-quinoline-4-carboxylic acid (α-methyl-δ-diethylaminobutyl)amide were dissolved in 2300 ml of acetone, then 1 g of activated carbon was added, and the mixture was boiled for 10–15 minutes. The solution was filtered, cooled, and 2–3 ml of hydrochloric acid were added (d 1.179). The resultant precipitate was filtered off, washed with acetone and dried at 80°–90° C. The yield of 2-[2′-(5″-nitrofuryl-2″)vinyl]quinoline-4-carboxylic acid (α-methyl-δ-diethylaminobutyl)amide chloride was 3.6 g (74.1%), m.p. 183°–187° C. (with decomposition).

Analysis, %: C 61.56; H 6.62; N 11.38; Cl 7.05; $C_{25}H_{30}N_4O_4.HCl$. Theory, %: C 61.66; H 6.42; N 11.51; Cl 7.28.

EXAMPLE 14

2-[2′-(5″-nitrofuryl-2″)vinyl quinoline]-4-carboxylic acid (α-methyl-δ-diethylaminobutyl)amide dibromide was prepared as described in Example 13 from 2-[2′-(5″-nitrofuryl-2″)vinyl]quinoline-4-carboxylic acid (α-methyl-δ-diethylaminobutyl)amide and hydrobromic acid. The yield was 76.3%, m.p. 238°–240° C. (with decomposition).

Analysis %: C 48.98; H 5.21; N 9.36; Br 23.94; $C_{25}H_{30}N_4O_4.2HBr$. Theory %: C 49.11; H 5.28; N 9.11; Br 24.14.

What is claimed is:

1. Substituted 2-[2′-(5″-nitrofuryl-2″)vinyl- and 4′-(5″-nitrofuryl-2″)-1,3-butadienyl]quinoline-4-carboxylic acid amides of the formula

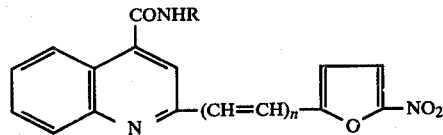

wherein
R=—$CH_2CH_2CH_2OH$;
—$CH(CH_3)(CH_2)_3N(C_2H_5)_2$
h=1, 2
and salts thereof.

2. A pharmaceutical composition useful as a contact-action antiblastic agent comprising, as the active ingredient, an antiblastic contact-action effective amount of a compound of the formula:

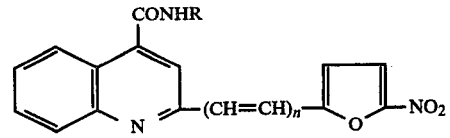

wherein R is —$CH_2CH_2CH_2OH$ or —$CH(CH_3)(CH_2)_3N(C_2H_5)_2$ and n is 1 or 2, or a salt thereof, in admixture with a pharmaceutically-acceptable liquid carrier.

3. A method of treating a warm blooded animal afflicted with one of the following malignancies: Ehrlich ascitic tumor, meloma B16, sarcoma AK, acatol-1, sarcoma 180, adenocarcinoma 755 or lymphatic leukemia L5178; which comprises intraperitoneally administering to said warm blooded animal an antiblastic effective amount of a compound as defined in claim 1.

* * * * *

UNITED STATES PATENT AND TRADEMARK OFFICE
CERTIFICATE OF CORRECTION

PATENT NO.   : 4,201,784

DATED        : May 6, 1980

INVENTOR(S)  : Nina Mikhailovna, et al

It is certified that error appears in the above—identified patent and that said Letters Patent is hereby corrected as shown below:

On the title page, below the Abstract, "No Drawings" should read -- 3 Drawing Figures --

Figure 2:
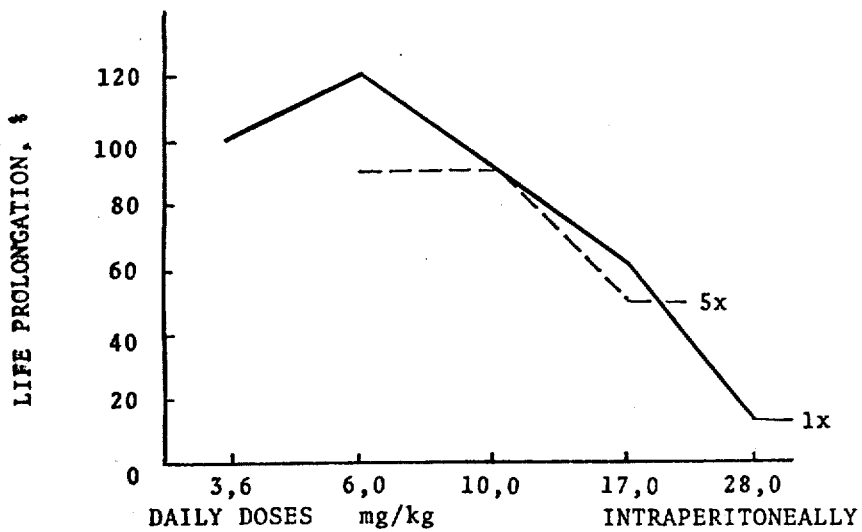
Figure 3:
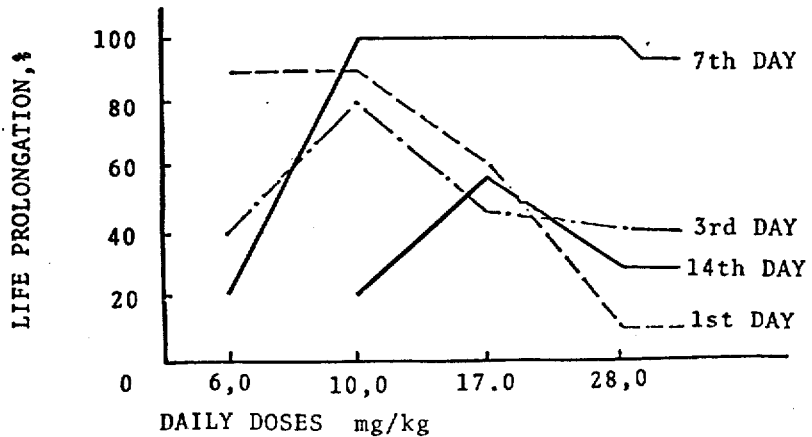

The attached sheet of drawings containing figs. 1 - 3 should be inserted as part of the above-identified patent.

*Signed and Sealed this*

*Twenty-second* Day of *July 1980*

[SEAL]

*Attest:*

SIDNEY A. DIAMOND

*Attesting Officer*     *Commissioner of Patents and Trademarks*